United States Patent [19]

Pecen et al.

[11] Patent Number: 5,083,035
[45] Date of Patent: Jan. 21, 1992

[54] POSITION LOCATION IN SURFACE SCANNING USING INTERVAL TIMING BETWEEN SCAN MARKS ON TEST WAFERS

[75] Inventors: Jiri Pecen, Palo Alto; Kenneth P. Gross, San Carlos; Brian Leslie, Cupertino; George Kren, Los Altos Hills, all of Calif.

[73] Assignee: Tencor Instruments, Mountain View, Calif.

[21] Appl. No.: 553,861

[22] Filed: Jul. 17, 1990

[51] Int. Cl.⁵ ............................................. G01N 21/86
[52] U.S. Cl. ..................................... 250/561; 250/571
[58] Field of Search ............... 250/234, 235, 236, 561, 250/571; 356/429

[56] References Cited

U.S. PATENT DOCUMENTS 4,329,011 5/1982 Mori et al. ........................... 250/236
4,404,596 9/1983 Juergensen et al. ................. 358/293

Primary Examiner—David C. Nelms
Assistant Examiner—K. Shami
Attorney, Agent, or Firm—Schneck & McHugh

[57] ABSTRACT

A particle imager and method for imaging particles on surfaces of substrates. A surface is raster scanned by a collimated light beam and particles on the surface are detected by the scattered light caused by the particles. During a scan path the intensity of the scattered light is measured forming intensity traces and location addresses for the detected particles. Data from each scan path is stored in memory. The imager is pre-calibrated with a test wafer having light scattering marker points spaced at known positions thereon. Scanning the test wafer, a clock measures time elapsed from a start position to each marker point. The corresponding elapsed times and known address locations are stored in memory for reference during data collection.

10 Claims, 3 Drawing Sheets

POSITION LOCATION IN SURFACE SCANNING USING INTERVAL TIMING BETWEEN SCAN MARKS ON TEST WAFERS

TECHNICAL FIELD

The present invention relates to the scanning of surfaces with a light beam, and in particular to the determination of the position of the beam on a surface during a scan.

BACKGROUND ART

In scanning generally flat surfaces for flaws, defects, particles and the like, a scanning beam originates from an apparent spot source, such as a reciprocating mirror or rotating polygon, i.e. an optical scanner. The scanner directs a scanning beam in an arc, but the surface prevents the scanning beam from traversing a true arc-like trajectory. If the beam had traversed a true arc, the determination of the beam position would be a simple matter. But when the beam traverses a plane the beam appears to travel faster at distances further away from the scan center. In many applications it is important to know the precise beam position. For example, in particle detection, particle position on a surface may be found only if the beam position is known. In the past, beam position could be estimated by knowing the position of the scanner and then calculating where beam should be on a surface. However, such calculations usually do not take into account factors such as wear on the scanner which cause errors relative to a theoretical scan path.

In the prior art, others have realized that scanner error creates a problem which must be corrected for precise particle or flaw position determination. For example, in U.S. Pat. No. 4,404,596 Juergensen et al. correct positional error due to uneven surfaces of a rotating polygonal mirror. While many of the prior art approaches have proved to be quite valuable, there is an ever greater need for precision, especially in locating dirt particles in ultraclea surfaces, such as semiconductor wafers. In wafer inspection, non-imaging particle detectors have been invented which accurately signal the presence of micron size particles and smaller. Mapping the location of such particles is needed to be able to predict whether circuits built on such a substrate will fail due to particle presence in a particular location.

An object of the invention is to increase the precision by which the location of a scanning beam on a surface may be determined.

SUMMARY OF THE INVENTION

The above object has been achieved in a beam scanner by clocking the beam relative to a known starting position and establishing known beam locations for subsequent clock intervals. A test wafer is manufactured with a plurality of light scattering elements disposed along a beam scan path. The scattering elements are very small pits or bumps spaced at equidistant positions along the scan path. A plurality of such paths are defined across the wafer surface so that at various scan paths across the wafer surface, the beam position may be clocked. The known starting location is a fixed pin or depression which gives a strong light scattering signal. A second pin may be placed opposite the first on the other side of the scan path for bidirectional scanning.

Once a strong light scattering signal is received from the pin marking the beginning of a scan, a high frequency clock is started. Each time one of the equidistant light scattering elements is encountered in the scan path, as indicated by a light scattering signal, the clock pulse count is stored at an address in a computer memory. Memory addresses correspond to physical locations of the light scattering elements. In other words, the computer memory contains addresses corresponding to each light scattering element position. With each address is associated a number indicative of the clock pulse count from the beam scan starting position.

Once the memory has been loaded with data from the test wafer, a target wafer is substituted for the test wafer. The scanning beam must pass over the start of scan marker in order to initiate the clock. Then, as clock pulses are counted, those counts, which correspond to the previously measured counts, signal the arrival of the beam at a position corresponding to the equidistant light scattering elements on the test wafer. Particles observed between light scattering elements may be located by interpolation.

After a number of hours of scanner operation, the test wafer is again used to generate a set of clock pulse data to be loaded into memory. In this way, even very small amounts of wear on scanner mechanical parts will not effect the precise determination of beam position location. In bidirectional scanning, the same procedure is used in each scanning direction, both with a test wafer and with a target wafer. A different set of clock data is generated for each scan direction.

BEST MODE FOR CARRYING OUT THE INVENTION

Figure 1:
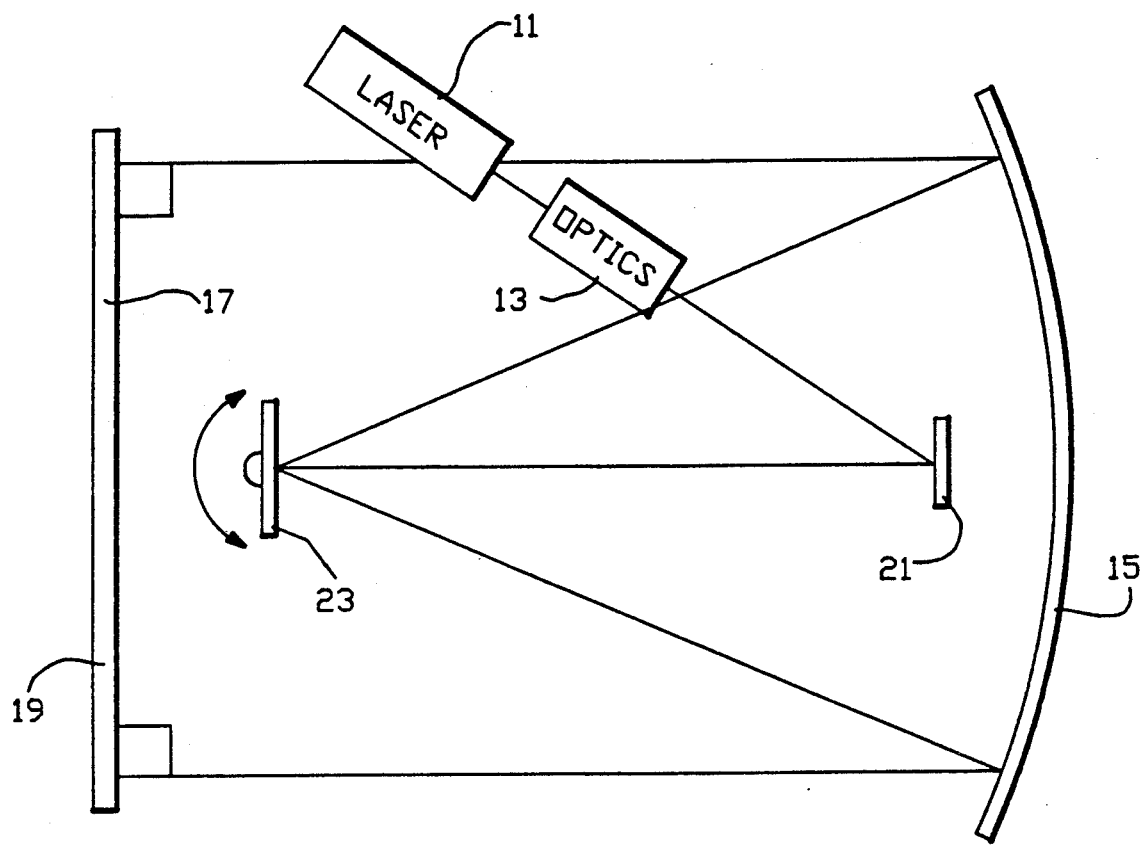
FIG. 1 is a plan view of an optical configuration for generating a scanning beam in accord with the present invention.

With reference to FIG. 1, laser 11, a low power helium-neon or argon ion laser generates a beam which is prefocused by optical elements 13, typically one or more lenses, to a point beyond the spherical mirror 15, namely the surface 17 of a wafer 19 being inspected. After passing through optics 13, the laser beam impinges upon a small fixed mirror 21 which folds the light path and directs the beam toward scanning mirror 23. The scanning mirror 23 is supported on an arm connected to a motor which rocks the mirror at its natural frequency of vibration. Such mirrors are known as resonant scanning mirrors and the natural frequency of vibration is specified by the manufacturer.

The scanning mirror is aligned at a slight tilt relative to the incident beam so that the scanning beam describes a shallow cone in space, but will follow a straight line path after reflection from the spherical mirror 15. The purpose of the spherical mirror's curvature is to cancel the effective field curvature of the prefocused beam to produce an essentially planar image field at surface 17. The scanning mirror 23 is optically flat and its axis of rotation is not perpendicular to the incoming beam in order to generate the shallow cone in the reflected beam, previously mentioned. This optical arrangement permits generation of a 100 micrometer scan spot on a flat image field with a path straightness within 10 micrometers over a total scan distance of 200 millimeters. The scan is nearly telecentric. A system with a focal length of about 500 millimeters should scan a 200 millimeter path. At a wavelength of 488 nanometrs and a final spot size of 100 micrometers diameter, where the beam diameter is measured at $1/e^2$, the beam diameter would be 16.3 millimeters at the scan mirror 23. While some aberration may be expected, the maximum aberration blur diameter is under 10 micrometers for astigmatism and under 4 micrometers of tangential coma, small enough relative to a 100 micrometer spot diameter to reduce the spot center intensity only a few percent. The estimated deviation from true telecentric scanning is from 1 milliradian to less than 40 milliradians.

Figure 2A:
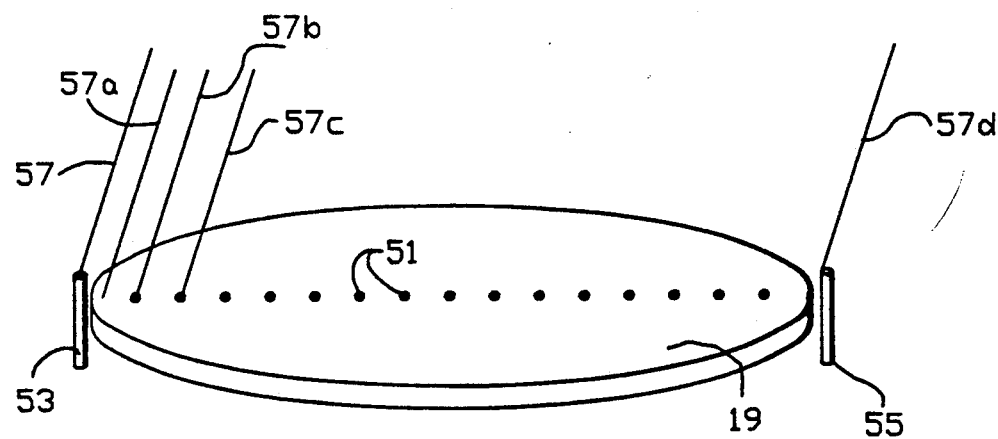
FIG. 2A is a perspective view of a wafer having equidistant light scattering elements.
Figure 2:
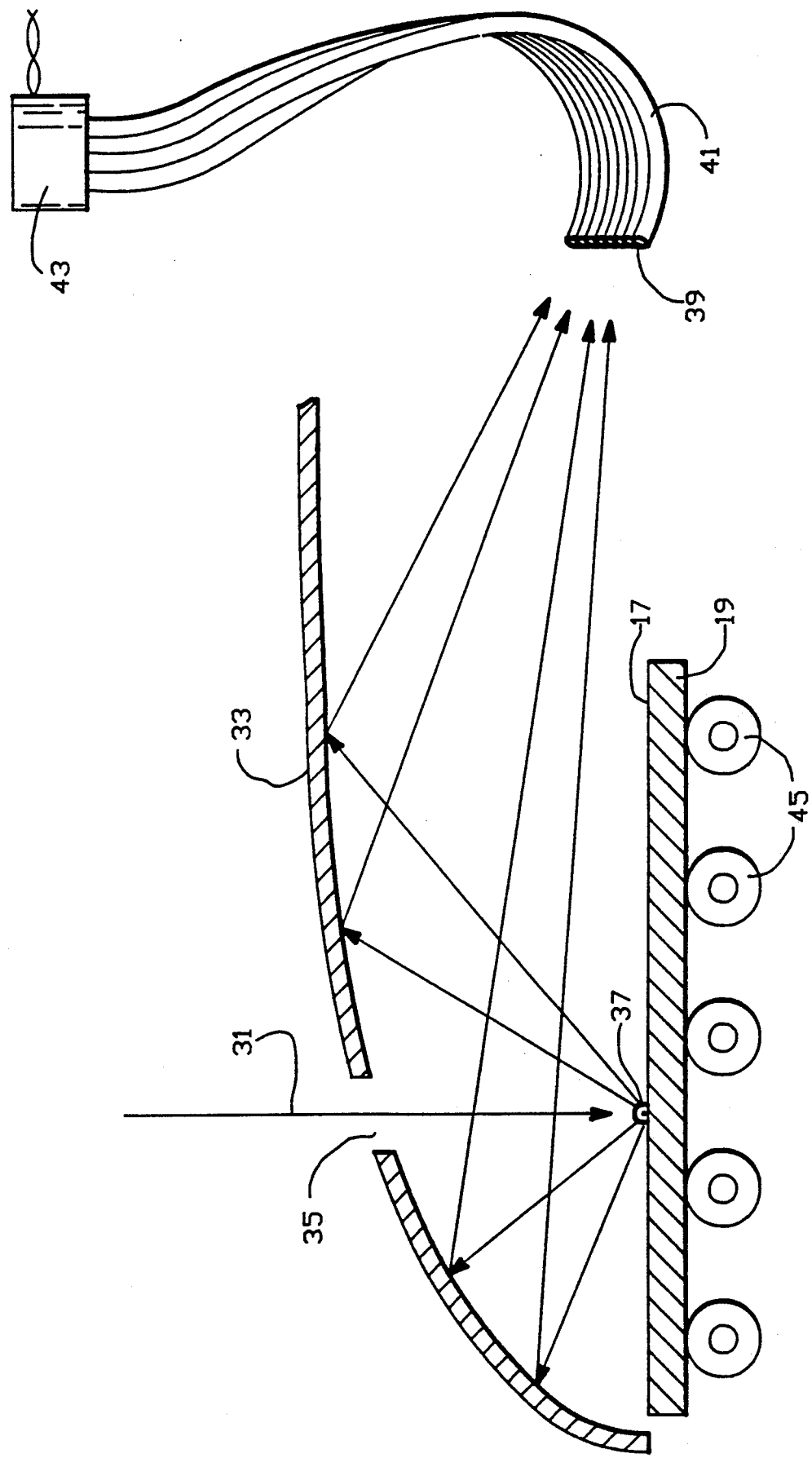
FIG. 2 is a plan view of an optical arrangement for collecting light from the apparatus of FIG. 1.

With reference to FIG. 2, a telecentric input beam 31 is seen passing into an internally reflecting elliptical cylinder 33 through a linear slot 35 whose length is parallel to the scan direction, i.e. in a plane perpendicular to the paper of the drawing. The narrow slit 35 allows egress of light specularly reflected from the reflective surface 17 of wafer 19. Beam 31 impinges along a focal line 37 extending into and out of the plane of the paper of the drawing. Focal line 37 is one of two foci of the elliptical cylinder 33. The second focal line 39 is a line where input ends of fiber optic fibers 41 are aligned. Thus, any light which is scattered from a dirt particle or flaw along the scanning line 37 will be reflected to the second scan line 39 and be input into fibers 41. Since the scattering is coming from irregular surfaces, the light appearing line 39 does not form a true optical image of the particle or flaw. Rather, the light along line 39 is representative of the scattered intensity from the particle or flaw. If the particle or flaw is large, more light will be scattered than if the particle is small. Light entering the fibers 41 is transmitted to a detector 43 which may be a photomultiplier tube. After a wafer is scanned along a line, the wafer is advanced slightly by wheels 45 or by another support mechanism. By slightly advancing the wafer, another line may be scanned. By scanning different lines which are parallel and slightly spaced apart, an entire wafer may be scanned. Differences between small particles and flaws such as cracks or spurious signals such as noise may be interpreted in accord with the particle detection method set forth in U.S. Pat. No. 4,766,324 to S. Saadat et al., assigned to the assignee of the present invention.

With reference to FIG. 2A, a wafer 19 is shown with a plurality of sampling points at which the scattered signal is sampled on the wafer. The wafer is placed between light marker pins 53 and 55 at opposite sides of the wafer and aligned with the scanning line of the optical system. As beam 57 is swept across the wafer, the amplitude of the scattered signal is sampled at specific positions 57a, 57b, 57c so as to cover the wafer with a regular array of sampling pints 51 which are preferably spaced a uniform distance apart. The start of the array is referenced to the marker pins 53 and 55.

The start of the array is timed to coincide with the transit of the beam across one of the marker pins (say 53) as the beam moves toward the other marker pin 55. The start signal is produced by a light detector placed behind either marker which senses the transit of the beam across the timing marker. When light from the beam is first received at the detector behind marker 53, as the beam passes over the edge of pin 53, it initiates a counter which counts pulses from an accurate 50 megahertz clock.

The output of the counter is continuously compared to a series of predetermined values which are stored in a random access memory. When the counter value equals the stored value, a pulse is issued to the sampling circuit which samples the instantaneous amplitude of the scatter signal received at the detector. The predetermined values which are compared to the counter output are selected so that the scatter signal is sampled at precisely equal distances apart or known positions on the wafer under test. The separation between sampling points is approximately 26 microns.

Any errors in position of the sampling points can be corrected by calibrating the position of the beam with respect to the marker pins using a standard wafer having scattering sources whose relative positions are known to very high accuracy. The apparent position of these scattering sources is measured using the initial table of sampling points. The difference between the apparent positions and the known positions of the scattering sources is used to generate an error function which is used to modify the predetermined values which are stored in the random access memory. This generates a new table of predetermined values which corrects for irregularities in the motion of the beam and defines the position of the sampling points to the same accuracy as the reference scattering sources on the standard wafer.

By this means one is able to establish a very accurate coordinate system in the X axis where the exact position of a scattering source on a wafer under test is known simply by counting the number of sample points from the start of the marker pin 53 or 55.

The Y position is established by counting the number of sweeps from the start of the wafer. This establishes an orthogonal set of XY coordinates which allows one to access and store data from any point of the wafer and store a microscan of a small section of the wafer in that area, without incurring any distortion of the stored image.

Figure 3:
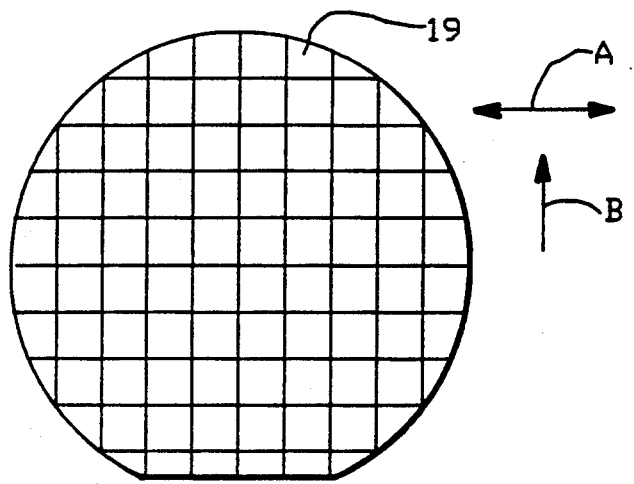
FIG. 3 shows a wafer having a grid-like pattern indicative of the location of light scattering elements.

With reference to FIG. 3, a wafer 19 is seen having an imaginary grid pattern thereon. Lines of the grid parallel to the line A represent scan lines. Actual scan lines are spaced by 10 microns, with the beam scanning in both directions. The wafer is advanced in the direction indicated by the arrow B by a wafer transport so that one scan line after another traverses the wafer surface. Thus, the scan mirror 23 achieves scanning in the direction indicated by arrow A while a wafer transport provides motion to the wafer so that the wafer is also scanned in the direction indicated by arrow B. The grid pattern of FIG. 3 has no physical meaning apart from showing scan direction.

Figure 4:
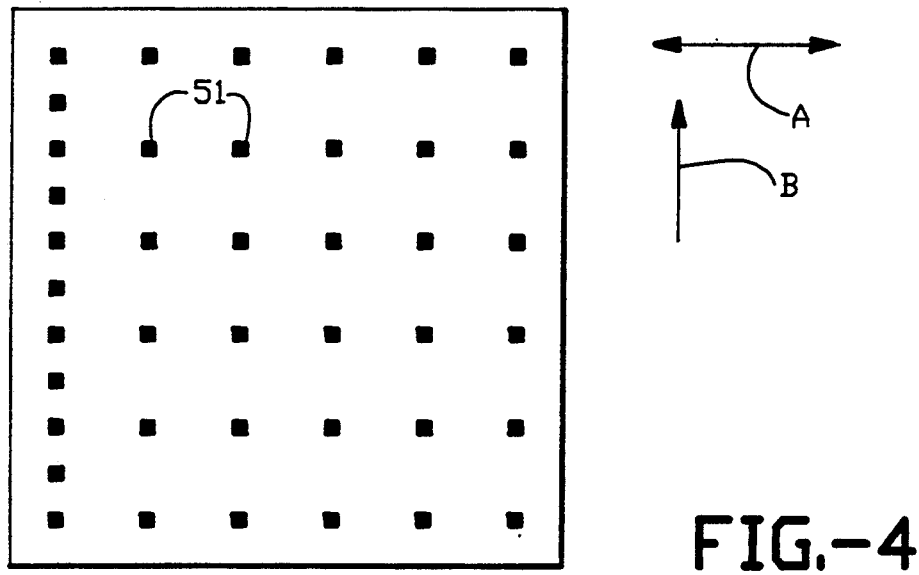
FIG. 4 is a detail from FIG. 3, showing light scattering elements.

FIG. 4 shows an array of equidistant sample points 51 on a small portion of a standard wafer. The center-to-center spacing of the points is 26 microns, while the scan line to scan line spacing is 10 microns. For greater throughput, the scan spacing may be increased, with some loss of resolution.

By timing the beam traverses between pins, the scanner amplitude may be adjusted to provide for a constant time of traverse between the pins. The scanner is tolerant to some amount of variation in its natural frequency of vibration, usually up to 2%. This is sufficient to allow precise adjustment of the scan time so that constant times are obtained between pins.

The signal going to detector 43 may be adjusted to correct for variations in the laser output power. This may be done by calibrating the detector for a number of decades of dynamic range with respect to scattering from a marker pin. For example, the three top decades of dynamic range for photomultiplier tube gain may be recorded. To record further levels, the incoming beam may be attenuated by a known amount using a neutral density filter. Such a filter could absorb most of the scattered light from a light scattering element. The amount absorbed would be set so that the detected signal is below the lowest decade of dynamic range measured without the filter. Thus, another few levels of dynamic range of the detector may be established, allowing the measurement of very small signals.

Figure 5:
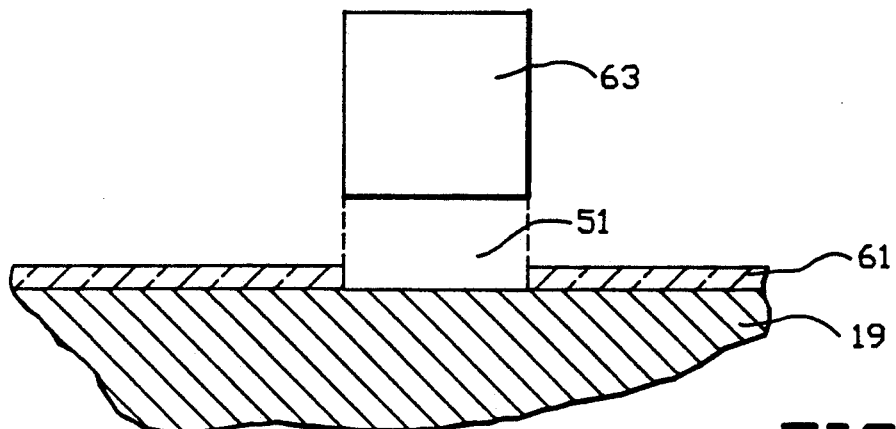
FIG. 5 illustrates the construction of a light scattering element in a semiconductor wafer.

The preparation of the light scattering elements in a test wafer is shown with reference to FIG. 5. Wafer 19 is coated with a thin layer of photoresist material 61. The wafer is patterned with a mask with openings formed at regions 51 by removal of material by photolithographic techniques. The square 63 represents material removed from a square opening, creating a light scattering element. As the scanning beam moves across the surface of material 61, it encounters the opening and the nonuniformity in the surface causes scattering. This technique is described further in U.S. Pat. No. 4,512,659 assigned to the assignee of the present invention.

We claim:

1. A method of determining the position of a scanning beam as it traverses a surface of a wafer in a path comprising:
   establishing a starting first location for a scan by positioning a scan start marker near an edge of a scan path,
   for a test wafer with optical marker points spaced at known locations across the wafer surface in said path, scanning the test wafer with scanning optics in a first scan and timing the beam from the scan start marker to each successive marker point, each of the marker points having a unique address,
   for each marker point address, storing in a memory the elapsed time from the start marker to the marker point address so that each address has a corresponding elapsed time associated therewith,
   for an unknown wafer, scanning the unknown wafer in a second scan using the same path and the sam scanning optics as said first scan and measuring the elapsed time from the scan start marker, and
   associating elapsed measured times corresponding to said stored addresses with beam position on the unknown wafer.

2. The method of claim 1 wherein establishing said starting location is by scattering light from a surface irregularity.

3. The method of claim 1 wherein establishing said starting location is by detecting the shadow of the marker on a detector placed behind the marker.

4. The method of claim 1 wherein said optical marker points on said test wafer are equidistantly spaced.

5. The method of claim 4 further defined by computing, for an ideal scanner, theoretical elapsed times at said equidistant marker points and comparing the theoretical elapsed times with actual measured elapsed times at marker points, the difference at each equidistant marker point indicating a difference between an ideal scanner and the actual scanner.

6. The method of claim 1 wherein locations of said optical markers are stored for equally spaced time intervals of a beam scan.

7. The method of claim 1 further comprising establishing a second starting location on an opposite side of a scan from the first starting location, the second starting location established by positioning a scan start marker near an edge of a scan path opposite the first edge.

8. The method of claim 7 wherein scatter data is collected from said unknown wafer with the laser beam moving alternately in both directions from first starting location to second starting location and from second starting location to first starting location.

9. The method of claim 1 further defined by using one or more markers to produce a reference scatter signal whose amplitude is used to control the gain of the detection system.

10. A method of determining the position of a scanning beam as it traverses a surface of a wafer in a path comprising,
    marking the starting edge of a scan path with a first light scattering feature,
    for a test wafer with equidistant optical scattering features spaced at known positions across the wafer surface in said path, scanning the test wafer with scanning optics in a first scan and timing the beam from the scan start marker to each successive scattering feature, each of the scattering features having a unique address,
    for each marker point address, storing in a memory the elapsed time from the start marker to the marker point address so that each address had a corresponding elapsed time associated therewith,
    for an unknown wafer, scanning the unknown wafer in a second scan using the same path and the same scanning optics as said first scan and measuring the elapsed time from the scan start marker, and
    associating elapsed measured times corresponding to said stored addresses with beam position on the unknown wafer.

* * * * *